United States Patent [19]

Ueno et al.

[11] Patent Number: 5,580,440

[45] Date of Patent: Dec. 3, 1996

[54] AIR FUEL RATIO SENSORY

[75] Inventors: Sadayasu Ueno, Katsuta; Norio Hasegawa, Mito; Naoki Minami, Katsuta; Kanemasa Sato, Katsuta; Shiro Oouchi, Katsuta, all of Japan

[73] Assignee: Hitachi, Ltd., Japan

[21] Appl. No.: 549,643

[22] Filed: Oct. 27, 1995

Related U.S. Application Data

[63] Continuation of Ser. No. 292,227, Aug. 22, 1994, abandoned.

[30] Foreign Application Priority Data

Aug. 20, 1993 [JP] Japan ................... 5-206225

[51] Int. Cl.⁶ ................................. G01N 27/26
[52] U.S. Cl. ............... 205/784; 205/784.5; 205/775; 205/782.5; 204/408; 204/425; 204/426; 204/427; 204/429; 123/672; 123/674; 123/676; 123/677; 123/693; 123/694; 123/510; 123/511; 73/23.21; 73/23.32; 73/31.04
[58] Field of Search ................. 204/408, 425, 204/424, 426, 427, 429, 421, 153.17, 153.16, 153.18, 153.1; 123/672, 674, 676, 677, 693, 694, 510, 511; 73/23.21, 23.32, 31.04

[56] References Cited

U.S. PATENT DOCUMENTS

| | | | |
|---|---|---|---|
| 4,419,211 | 12/1983 | Brauer | 204/408 |
| 4,753,209 | 6/1988 | Hibino et al. | 123/491 |
| 4,915,814 | 4/1990 | Harada et al. | 204/429 |
| 5,035,226 | 7/1991 | Nishikawa et al. | 123/494 |

FOREIGN PATENT DOCUMENTS

| | | |
|---|---|---|
| 60-128349 | 7/1985 | Japan . |
| 61-138155 | 6/1986 | Japan . |
| 62-198750 | 9/1987 | Japan . |
| 62-265560 | 11/1987 | Japan . |
| 1-159435 | 6/1989 | Japan . |
| 4-134152 | 5/1992 | Japan . |

Primary Examiner—Bruce F. Bell
Attorney, Agent, or Firm—Evenson, McKeown, Edwards & Lenahan P.L.L.C.

[57] ABSTRACT

A method and apparatus are disclosed for measuring atmospheric pressure in conjunction with an air-fuel ratio sensor of the type comprising a concentration cell with atmospheric air and exhaust electrodes on opposite sides of a solid-state electrolyte having oxygen ion conductivity. During an atmospheric pressure measuring cycle, oxygen ions are pumped from the atmospheric air electrode to the exhaust electrode, in a quantity which is either predetermined at a fixed value, or is sufficient to bring the cell to an equilibrium state. Atmospheric pressure is then calculated from measured emf of the cell, using an experimentally derived functional relationship. In a second embodiment, ions are pumped until a predetermined change of the concentration cell emf is achieved, and atmospheric pressure is determined based on the amount of time required to achieve such change. The atmospheric pressure measuring mode is operated on a time shared basis with the air-fuel ration detection mode.

17 Claims, 2 Drawing Sheets

AIR FUEL RATIO SENSORY

This application is a continuation of application Ser. No. 08/292,227, filed on Aug. 22, 1994 now abandoned.

BACKGROUND OF THE INVENTION

The present invention relates to a sensor for detecting the input air-fuel ratio of an internal combustion engine from the oxygen and unburned gas composition in the exhaust gas of the engine.

A known air-fuel ratio sensor arrangement, such as disclosed, for example, in Japanese Patent Application Laid-Open No. 60-128349 (1985), Japanese Patent Application Laid-Open No. 61-138155 (1986), Japanese Patent Application Laid-Open No. 62-265560 (1987), Japanese Patent Application Laid-Open No. 62-198750 (1987), Japanese Patent Application Laid-Open No. 4-134152 (1992) and so on, comprises a concentration cell having an atmosphere air side electrode which is exposed directly to atmospheric air, and an exhaust gas side electrode which is covered with an exhaust gas diffusion rate control member, the two electrodes being provided on opposite sides of a solid-state electrolyte having oxygen ion conductivity. Ion-pumping (hereinafter referred to as "pumping") of oxygen molecules is performed between the atmospheric air side electrode and the exhaust gas side electrode such that the electromotive force of the concentration cell due to the ratio of oxygen partial pressure induced between the atmospheric air side electrode and the exhaust gas side electrode is kept constant, and the oxygen concentration in the exhaust gas is detected from the pumping current.

Air-fuel ratio sensors of this type have an exhaust gas pressure dependence, as discussed in T. Kamo, et al: Lean Mixture Sensor, SAE Paper 850380, (1985). According to this reference, the exhaust gas pressure dependence is classified based on the shape of the diffusion rate control member as follows:

1. In the case of a simple pore film: Diffusion is primarily molecular diffusion (exhaust pressure dependence is small);
2. In a case of a porous film: Diffusion is primarily Knudsen diffusion (exhaust pressure and pumping current are in a proportional relationship).

Actually, in both of the above cases, the exhaust gas pressure dependence of the output from the sensor is large enough to require correction.

Exhaust gas pressure dependence can be divided into two components: one being governed by engine parameters, and another governed by atmospheric pressure. The former may be estimated from engine parameters, while the latter dependence cannot be corrected unless atmospheric pressure is measured. The atmospheric pressure dependence is such that the air-fuel ratio sensor puts out a smaller value for the air-fuel ratio (rich side) than the demand value as the altitude becomes higher, due to the characteristic of the sensor.

Since such atmospheric (exhaust gas) pressure dependence of the air-fuel ratio sensor increases the error in the sensor output, it is necessary to correct the sensor output depending on the altitude (elevation correction). Therefore, in the past, atmospheric pressure has been measured by using a special-purpose atmospheric pressure sensor (for example, Japanese Patent Application Laid-Open No. 1-159435 (1989), Japanese Patent Application Laid-Open No. 4-134152 (1992)).

SUMMARY OF THE INVENTION

An object of the present invention is to provide a technology capable of detecting the atmospheric pressure by means of an air-fuel ratio sensor without any special-purpose atmospheric pressure sensor.

A further object of the invention is to provide a method and apparatus for correcting the output from an air-fuel ratio sensor having atmospheric pressure dependence and engine control parameter and the like, by using the above atmospheric pressure detecting technology.

These and other objects and advantages are achieved according to the invention by an air-fuel ratio detector of the generic type described above in which an atmospheric pressure measuring mode is provided separate from the air-fuel ratio detecting mode. Means are provided for detecting the electromotive force of the concentration cell due to the ratio of oxygen partial pressure induced between the atmospheric air side electrode and the exhaust gas side electrode (hereinafter, referred to as "electromotive force of concentration cell for measuring atmospheric pressure") by pumping oxygen molecules from the atmospheric air side electrode to the exhaust gas side electrode (either a predetermined amount, or an amount required to reach an equilibrium state), using pumping means provided in the atmospheric pressure measuring mode. The current atmospheric pressure is determined from the electromotive force of the concentration cell for measuring atmospheric pressure thus detected in the atmospheric pressure measuring mode, using an experimentally determined relationship between the atmospheric pressure and the electromotive force of concentration cell for measuring atmospheric pressure. The latter relationship is determined with varying atmospheric pressure by changing the altitudes.

In another embodiment of the invention means are provided to measure the time t required to pump the oxygen molecules from the atmospheric air side electrode to the exhaust gas side electrode until the electromotive force of concentration cell changes by a preset change value. Atmospheric pressure is calculated based on the time t measured in said atmospheric pressure measuring mode, and an experimentally determined relationship between atmospheric pressure and t. The latter relationship is determined with varying atmospheric pressure by changing the altitudes.

Before describing the key point of the present invention, the operating principle of a generic air-fuel ratio sensor of the diffusion rate control type is described below, referring to FIG. 1, which depicts an atmospheric air side electrode 1, a solid-state electrolyte 2 having ion conductivity, an exhaust gas side electrode 3, and a diffusion rate control member 4. The diffusion rate control member 4 is either a fine porous film or a simple pore member, which covers or envelopes the whole exhaust gas side electrode 3 to suppress the diffusing speed of the exhaust gas to the surface of the exhaust gas side electrode (that is, it controls the diffusion rate). A space 5 surrounds the exhaust gas side electrode. (When the exhaust gas side electrode is covered with a porous film, its pores themselves form the space 5, and when the exhaust gas side electrode is covered with a simple pore member, the space enveloped with the simple pore member forms the space 5.) The sensor cell composed of the solid-state electrolyte having electrodes can conduct a stable pumping current when it is heated using an adjacent heater.

The electromotive force E of the oxygen concentration cell between the respective electrodes 1 and 3 exposed to the atmospheric air and the exhaust gas is given by the Nernst equation shown by Equation 1.

$$E = (RT/4P)\ln(Pa/Pd) = 0.0496 \ln(Pa/Pd), \qquad (1)$$

where R is the gas constant; T is the absolute temperature of the cell (=1000 K.); F is the Faraday constant; Pd is the oxygen partial pressure around the exhaust gas side electrode; and Pa is the oxygen partial pressure around the atmospheric air side electrode.

The diffusion rate control member which covers the exhaust gas side electrode traps the exhaust gas for a time in the space 5. Ionization of oxygen contained in the exhaust gas is accelerated by the catalytic power of the platinum (electrode) near the condition of the theoretical (stoichiometric) air-fuel ratio, which causes a steep switching characteristic in the electromotive force as a function of the air-fuel ratio. With the oxygen around the exhaust gas side electrode continuously pumped to a thin state, the exhaust gas diffuses freely through the diffusion rate control member toward the exhaust gas side electrode. Oxygen molecules in the diffusion-rate-controlled exhaust gas are immediately ionized and pumped at the exhaust gas side electrode. The pumped oxygen ions are measured as a current (generally called a "pumping current" or "diffusion current"). Since the pumping current is proportional to the oxygen concentration in the exhaust gas (that is, the air-fuel ratio), the air-fuel ratio can be detected.

In other words, the oxygen molecules are ionized and pumped in such a manner that the electromotive force E of the concentration cell due to the oxygen partial pressure ratio produced between the atmospheric air side electrode and the exhaust gas side electrode is kept constant, and by measuring the pumping current the air-fuel ratio is detected in a wide range.

The diffusion flow rate of the exhaust gas is determined by the shape of the simple pore which controls diffusion, as given by Equation 2.

$$Ip = 4FD(Pe-Pd)/RT \times (s/l), \quad (2)$$

where Ip is oxygen diffusion current; D is the diffusion constant of the exhaust gas mixture (composed of various compositions); s/l is the ratio of the cross-sectional area s of the passage and the length of the passage when the diffusion rate control member is simulated by an equivalent single hole; and Pe is the oxygen partial pressure in the exhaust gas.

FIG. 1 shows a sensor of the type in which the oxygen ions in the diffusion-rate-controlled exhaust gas are conducted in either direction as the pumping current IP, such that the electromotive force E of the concentration cell produced by the oxygen concentration ratio between the atmospheric air side electrode 1 and the exhaust gas side electrode 3 during the normal air-fuel ratio detecting mode is maintained at a constant level. This is accomplished by controlling the drive voltage Vs with negative feedback (not shown in FIG. 1).

The pumping current Ip is controlled in such a manner that the electromotive force E of the concentration cell remains fixed, for example, at E=0.571 V (based on the Nernst Equation 1) under a constant operating condition such as temperature. In this time, the ratio between the oxygen partial pressure Pd in the exhaust gas side electrode and the oxygen partial pressure Pa in the atmospheric air side electrode always becomes pa/Pd=$10^5$. (That is, pa=$2.09 \times 10^{-1}$; pd=$2.09 \times 10^{-6}$.) In this arrangement, the air-fuel ratio can be obtained from the pumping current as described above.

The operation of the atmospheric pressure measuring mode according to a first embodiment of the present invention, will now be described. To detect atmospheric pressure, the sensor arrangement is shifted from the (normal) air-fuel ratio detecting mode to the atmospheric pressure measuring mode. In the atmospheric pressure measuring mode, a given pumping voltage Vs, having a polarity such that the atmospheric air side electrode is a negative (−) pole and the exhaust gas side electrode is a positive (+) pole, is applied between the atmospheric air side electrode and the exhaust gas side electrode to pump either a predetermined quantity Q of oxygen molecules from the atmospheric air side electrode to the exhaust gas side electrode, or a quantity of oxygen molecules necessary such as to reach the equilibrium state. For example, in the case of pumping a given amount Q of oxygen molecules, the control is performed as pumping current of 30 mA and pumping time of 6ms.

As a specific example, when pumping is performed-at the altitude of 0 m and under the standard atmospheric pressure Po (=101.3 kPa) such that the oxygen partial pressure becomes Pa/Pd–$10^2$, the electromotive force of the concentration cell E is 0.228 V, as determined from Equation 1.

When an altitude difference h is caused by moving of a vehicle, the atmospheric pressure, and consequently the oxygen concentration, in the vicinity of the atmospheric air side electrode change. The relation between the altitude and the atmospheric pressure can be expressed by Laplace atmospheric pressure altitude equation of Equation 3.

$$h = 18400(1+0.00366T) \log (Po/Ph), \quad (3)$$

where h is the elevation above sea level (m); T is the average temperature (°C.); Po is standard atmospheric pressure at sea level; and Ph is the atmospheric pressure at altitude h.

For example, since Ph=71.4 kPa at 20° C. at altitude of 3000 m, the oxygen concentration $Pa_p$ in the atmospheric air side electrode at altitude of 3000 m can be expressed by Equation 4.

$$Pa_p = 2.09 \times 10^{-1} \times 71.4/101.3 = 1.47 \times 10^{-1}. \quad (4)$$

The oxygen concentration $Pd_p$ in the vicinity of the exhaust gas side electrode at altitude of 3000 m after pumping a given amount Q of oxygen in the vicinity of the exhaust gas side electrode, as shown by Equation 5, becomes a nearly middle value between Pd and Pa at altitude of 0m.

$$Pd_p = 2.09 \times 10^{-3}. \quad (5)$$

Therefore, the electromotive force Ep of the concentration cell at altitude of 3000 m can be expressed by Equation 6.

$$\begin{aligned} Ep &= 0.0496 \ln(Pa/Pd) \\ &= 0.0496 \ln(1.47 \times 10^{-1}/2.09 \times 10^{-3}) \\ &= 0.211 V. \end{aligned} \quad (6)$$

That is, the electromotive force of the concentration cell is 0.228 V at altitude of 0m, and 0.211 V at altitude of 3000 m, a difference of 0.017 V. It can be understood from the difference that the electromotive force of the concentration cell has a correlation with (that is, it is proportional to) the altitude (atmospheric pressure). Therefore, by experimentally determining in advance, under atmospheric pressures of various altitudes, the correlation between i) the electromotive force of the concentration cell (in the atmospheric pressure measuring mode) when the oxygen molecules are pumped from the atmospheric air side electrode to the exhaust gas side electrode in the given amount Q, and ii) the atmospheric pressure, the atmospheric pressure can then be obtained by substituting the actual measured value of the electromotive force of the concentration cell detected in the atmospheric pressure measuring mode into the correlation. (It should be noted that the experimentally determined electromotive force of the concentration cell for measuring atmospheric pressure differs somewhat from the calculation because of the variations in individual sensors.)

When oxygen molecules are pumped from the atmospheric air side electrode to the exhaust gas side electrode until an equilibrium state is obtained (instead of pumping a predetermined quantity Q of oxygen molecules) the electromotive force of the concentration cell due to the oxygen partial pressure ratio between the respective electrodes since the equilibrium state reaches the condition in which the oxygen concentration around the both electrodes (between the atmospheric air side electrode and the exhaust gas side electrode) due to leakage of the oxygen molecules pumped into the vicinity of the exhaust gas side electrode into the exhaust gas through the diffusion rate control member in this case. Therefore, if the correlation between the electromotive force of the concentration cell and the equilibrium atmospheric pressure is determined in advance, the atmospheric pressure can now be obtained by substituting the electromotive force of concentration cell actually detected by the atmospheric pressure mode into the correlation function.

The correlation may be expressed as a mathematical function which is obtained from the experimentally determined relationship between the electromotive force of the concentration cell and the atmospheric pressure at equilibrium. (The details will be described in the experimental data of Table 2 in an embodiment.) The correlation can be expressed for example, by y=ax+b (a straight line, connoting direct proportionality), and the atmospheric pressure can thus be calculated by substituting the electromotive force of the concentration cell actually detected in the atmospheric pressure mode for x in the correlation.

On the other hand, the correlation can also be expressed in the form of a table which contains experimentally determined values for the electromotive force of concentration cell and the equilibrium atmospheric pressure. The atmospheric pressure can be obtained by retrieving the table data using the electromotive force of the concentration cell actually detected in the atmospheric pressure mode, and performing an interpolation when the electromotive force of concentration cell actually detected by the atmospheric pressure mode is between the table values.

In the second embodiment of the invention, oxygen molecules are pumped from the atmospheric air side electrode to the exhaust gas side electrode until the change of the electromotive force of concentration cell reaches a preset change value, using the pumping means in the atmospheric pressure measuring mode. Since the required pumping time t depends on and is proportional to the atmospheric pressure, the correlation between the atmospheric pressure and the time t can be obtained in advance by an experiment with varying atmospheric pressure by changing the altitudes. The atmospheric pressure now can be obtained by substituting the required time t actually detected by the atmospheric pressure mode into the correlation. The correlation is also expressed by a functional equation or by a table and an interpolation equation in the same manner as in the first embodiment of the invention.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
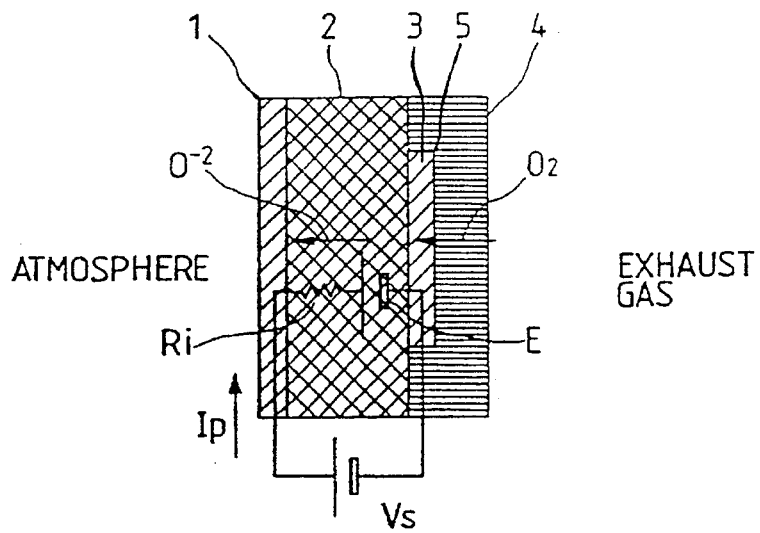
FIG. 1 is a schematic diagram which shows the operation principle of a diffusion rate control type air-fuel ratio sensor.

The present invention will now be described in detail below, referring to the drawings.

Figure 2:
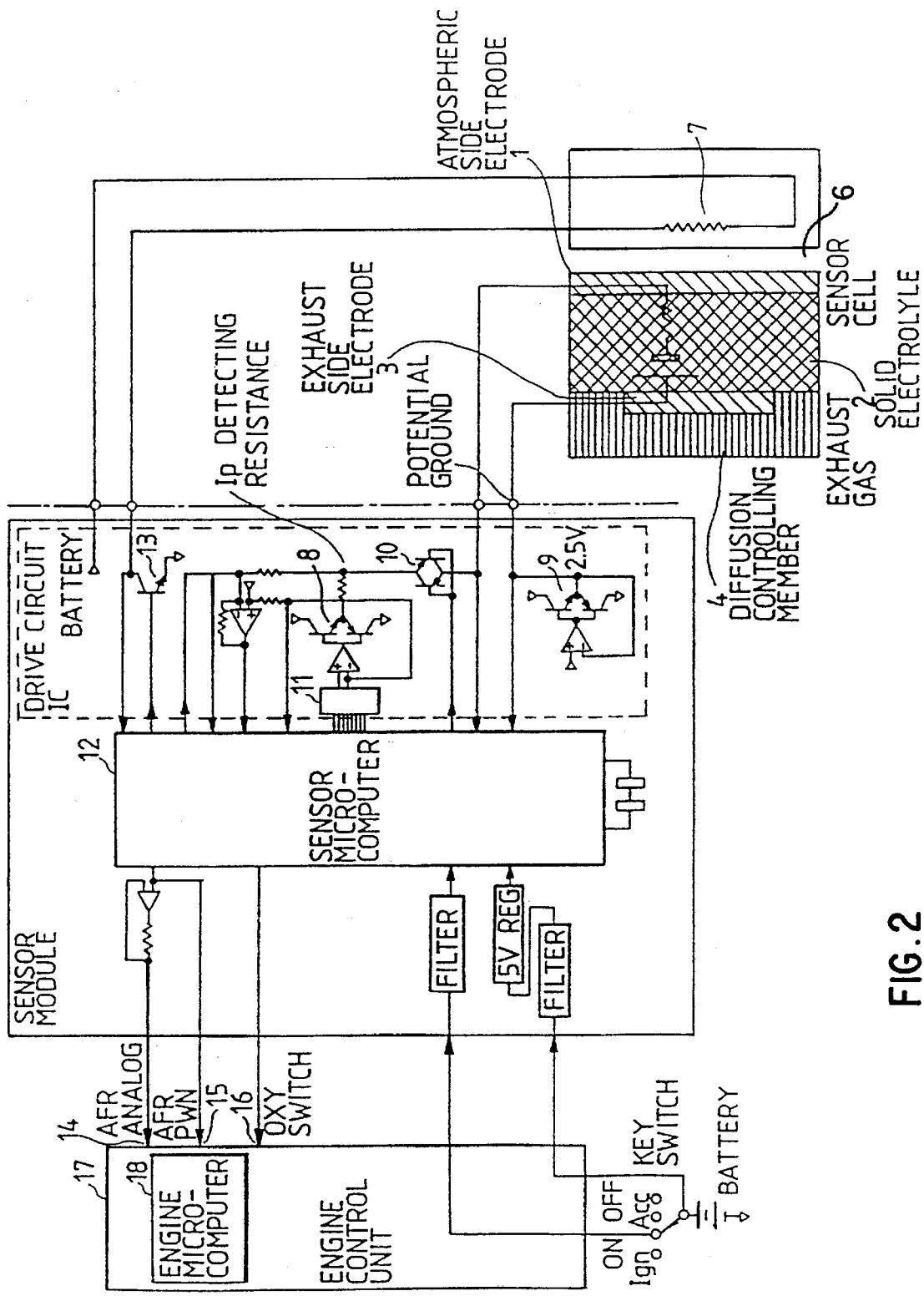
FIG. 2 is a circuit diagram showing an embodiment of the present invention.

FIG. 2 shows an embodiment of an air-fuel ratio sensor in accordance with the present invention, which comprises a solid-state electrolyte 2 having oxygen ion conductivity as shown in FIG. 1, an atmospheric air side electrode 1 provided on one surface of the solid-state electrolyte 2 (a surface exposed to the atmospheric air), an exhaust gas side electrode 3 provided on the other surface (exposed to the exhaust gas environment of an engine), an exhaust gas diffusion rate control member 4 covering the exhaust gas side electrode 3, and a heater 7 to maintain the solid-state electrolyte 2 at a given activated temperature. The sensor cell 6 is an oxygen concentration cell having a function to control the exhaust gas diffusion rate.

The numerals 8 and 9 are current drive circuits for conducting the diffusion current (pumping current) Ip of controlled diffusion rate in the sensor cell 6 in either direction, the numeral 10 being a semiconductor switch for switching on and off the current, the numeral 11 being a D/A converter, the numeral 12 being a micro-computer which performs a normal air-fuel ratio detecting mode as well as an atmospheric pressure measuring mode. The electromotive force (voltage between the electrodes) E of the oxygen concentration cell 6 is detected; the diffusion current Ip is controlled such that the electromotive force E of the concentration cell follows a given value; and the drive voltage Vs required to conduct the current is calculated. The D/A converter 11 reads out the values Ip and Vs and converts them from digital signals to analog signals.

The numeral 13 is a transistor which controls the heater to maintain the temperature of the sensor cell 6 at a constant level with negative feed-back control by obtaining the resistance R1 between the electrodes in the sensor cell 6 using the micro-computer 12. The output signals for the air-fuel ratio sensor obtained with the micro-computer 12 are an analog output 14, a pulse width modulation (PMW) output 15, and a switching output 16 at the theoretical air-fuel ratio point, being the same as that for an oxygen sensor.

In the normal air-fuel ratio detecting mode, in a cycle of 8 ms the micro-computer 12 detects the electromotive force E of concentration cell produced by the oxygen partial pressure ratio between the atmospheric air side electrode 1 and the exhaust gas side electrode 3, controlling the current drive circuits 8 and 9 with negative feed-back control in order to keep the electromotive force E at a constant level by ionizing the oxygen molecules in the exhaust gas of controlled diffusion rate and conducting the ions as the pumping current Ip, in either direction.

For example, as described previously in the discussion of the operation of the invention, the pumping current Ip is controlled to flow in either direction such that the electromotive force E is maintained at E=0.57 IV based on the Nernst Equation 1 under a constant operating condition such as temperature. At this time, the ratio of the oxygen partial pressure at the atmospheric air side electrode and the oxygen partial pressure in the vicinity of the exhaust gas side electrode 3 becomes Pa/Pd=$10^5$ (Pa=$2.09\times10^{-1}$; pd=$2.09\times10^{-6}$). The air-fuel ratio can be obtained from the pumping current Ip.

In the atmospheric pressure measuring mode (for example, with a cycle of 1s), the given quantity Q of oxygen is pumped from the atmospheric air side electrode 1 to the exhaust gas side electrode 3 using the current drive circuits 8 and 9 by processing the interrupt of the atmospheric pressure measuring mode by saving the air-fuel ratio detecting mode of 8 ms cycle. Then, the electromotive force E of the concentration cell just after pumping (electromotive force of concentration cell for measuring atmospheric pressure) is measured.

The micro-computer 12 then calculates the atmospheric pressure by substituting the electromotive force of the concentration cell for measuring atmospheric pressure actually detected in the atmospheric pressure measuring mode into the experimentally determined correlation function between the atmospheric pressure and the electromotive force of concentration cell for measuring atmospheric pressure. The actual correlation will be described later, referring to Table 2.

Figure 3:
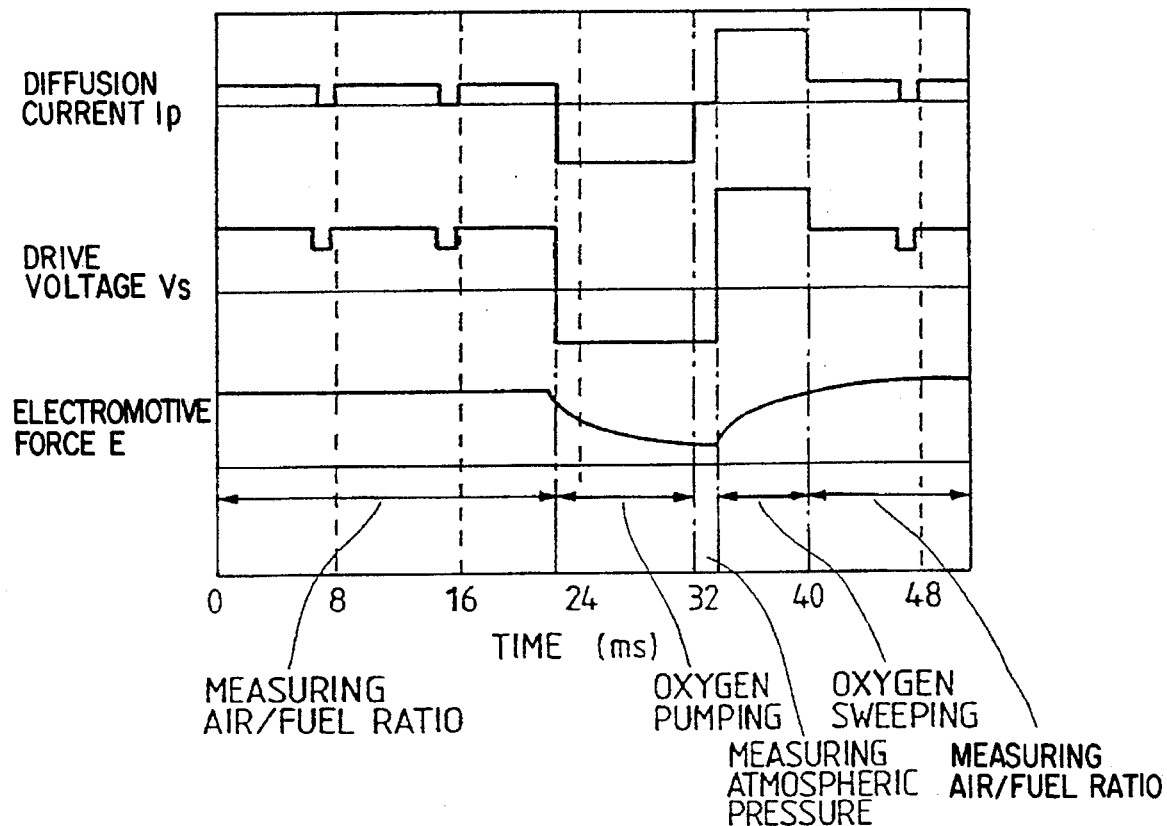
FIG. 3 is a time chart showing the air-fuel ratio detecting mode and the atmospheric pressure measuring mode in the above embodiment.

FIG. 3 shows the drive sequence of the atmospheric pressure measurement using the air-fuel ratio sensor, including the electromotive force E of the concentration cell, the pumping current (diffusion current) IP between the electrodes, and the power source voltage Vs for the current Ip drive.

Here, the principle of the correlation will be described.

Table 1 shows the relationship (obtained by calculation) between the oxygen partial pressure Pd, after the given quantity Q of oxygen molecules have been pumped from the atmospheric air side electrode 1 to the vicinity of the exhaust gas side electrode 3 (pumping current of 30 mA, pumping time of 8 ms), and the electromotive forces Ep of the concentration cell for altitudes of Om and 3000, as well as the difference between the electromotive forces at these altitudes. The calculation is carried out in the manner described previously in the description of the operation of the invention.

TABLE 1

| Pd | EMF E (V) (Altitude Om) | EMF E$^p$ (V) (Altitude 3000 m) | EMF DIfference (V) |
|---|---|---|---|
| $2.09 \times 10^{-6}$ | 0.571 | 0.554 | 0.017 |
| $2.09 \times 10^{-5}$ | 0.457 | 0.440 | 0.017 |
| $2.09 \times 10^{-4}$ | 0.343 | 0.326 | 0.017 |
| $2.09 \times 10^{-3}$ | 0.228 | 0.211 | 0.017 |
| $2.09 \times 10^{-2}$ | 0.114 | 0.097 | 0.017 |

Note: Pa = $2.09 \times 10^{-1}$

In the air-fuel ratio detecting mode, the oxygen partial pressure in the vicinity of the exhaust gas side electrode is set in Pd=$2.09\times10^{-6}$. (The oxygen partial pressure Pa of the atmospheric air side electrode is $2.09\times10-1$.) On the other hand, in the atmospheric pressure measuring mode, the value of the oxygen partial pressure in the vicinity of the exhaust gas side electrode is set in. Although in the discussion of the operation of the invention above Pd=$2.09\times10^{-3}$, the electromotive force E is apt to saturate at approximately 0.4 V due to the oxygen leakage to the exhaust gas side through the pores in the vicinity of the exhaust gas side electrode when pumping is actually performed.

Next, table 2 shows the experimentally determined correlation between atmospheric pressure and the electromotive force Ep of the concentration cell. The experimental data in Table 2 show the electromotive forces Ep for atmospheric pressures at various altitudes and the differences between the electromotive force at altitude of Om and at altitude at 3000 m.

TABLE 2

| Atmospheric pressure (kPa abs.) | Altitude (m) | EMF $E_p$ (mV) Max.–Min. | Altitude Om-3000 m EMF Diff. (mV) |
|---|---|---|---|
| 0.0 | 0 | 30.7– | 0.0 |
| 10.0 | 750 | 27.9–26.3 | 3.6 |
| 13.3 | 998 | 26.2–24.7 | 5.3 |
| 20.0 | 1500 | 28.1–23.8 | 6.3 |
| 26.7 | 2003 | 23.0–21.4 | 8.5 |
| 33.3 | 2498 | 19.5–17.5 | 12.2 |
| 40.0 | 3000 | 16.1–14.3 | 15.5 |
| 53.3 | 3998 | 8.1–6.0 | 23.6 |
| 60.8 | 4560 | 2.5–1.2 | 28.9 |
| 101.3 | 7598 | –0.0 | 30.7 |

Note: Ip = 30 mA, t = 8 ms constant

According to Table 2, the difference of electromotive force in an altitude of 3000 m is actually measured as 15.5 mV which is confirmed to be the approximated value of 17 mV in Table 1.

Therefore, by using the relationship between atmospheric pressures at various altitudes and the electromotive force Ep obtained from the experiment, the atmospheric pressure can be detected by substituting the electromotive force Ep actually detected in the atmospheric pressure measuring mode into this relation.

There are, of course, various methods of detecting the atmospheric pressure. For example:

(1) A table is formed using the experimental data as shown in Table 2 (atmospheric pressure-electromotive force or atmospheric pressure-difference of electromotive force) and stored in a micro-computer, and the electromotive force Ep of the concentration cell actually detected in the atmospheric pressure measuring mode is searched in the table to retrieve a corresponding atmospheric pressure. (In this case, when the electromotive force Ep of concentration cell is between the two values in the table for the electromotive force of concentration cell, the atmospheric pressure is calculated by interpolation.)

(2) A mathematical function expressing the relationship is formed using the experimental data as shown in Table 2 of atmospheric pressure-electromotive force or atmospheric pressure-difference of electromotive force data. (The relationship between them is approximately proportional and therefore can be expressed as a linear function.) The electromotive force or the difference of the electromotive forces of concentration cell actually detected in the atmospheric pressure measuring mode is then substituted into the above functional equation to calculate the corresponding atmospheric pressure.

(3) Since the ratio Ep/$Ep_0$ of the electromotive force of the concentration cell at an altitude Ep and the standard electromotive force of the concentration cell at altitude Om, $EP_0$ becomes a normalized atmospheric pressure signal, the atmospheric pressure can be calculated from the correlation between the atmospheric pressure and Ep/$Ep_0$. Such a caculating function is performed in the micro-computer 12.

The interruption cycle of the atmospheric pressure detecting process (atmospheric pressure measuring mode) is determined by the degree of responsiveness required in the case of a change in the atmospheric pressure during an ascending or descending state. For example, when the air-fuel ratio detecting cycle is constant at 8 ms, the atmospheric pressure detecting cycle is probably within the range of 0.1 s to 500 s. The interruption may be performed according to a fixed cycle, or may be initiated in response to detecting an ascent or descent. Because the cycle and timing have no negative effect on the air-fuel ratio detecting function, the atmospheric pressure detecting function can be accomplished.

Although a specific process may be provided for the oxygen pumping current in the atmospheric pressure measuring mode, oxygen pumping may also be processed, for example, after measuring the resistivity between the electrodes utilizing the current measured in the air-fuel ratio detecting process. In this manner, the cycle for atmospheric pressure detection can be shortened relative to the cycle for the air-fuel ratio detection if necessary.

Concerning the algorithm for the atmospheric pressure measuring mode, a first method has been described in the above embodiment. That is, a given quantity Q of oxygen (or alternatively, the amount of oxygen necessary to reach the equilibrium state, as described in the discussion of the operation of the invention) is pumped from the atmospheric air side electrode to the exhaust gas side electrode, and the electromotive force of the concentration cell measured at that time is applied to the given correlation to detect the atmospheric pressure corresponding to the altitude.

Another applicable method is that the atmospheric pressure can be calculated from the time required to generate a given electromotive force by pumping oxygen ions from the atmospheric air side to the exhaust side electrode. That is, a predetermined constant pumping drive voltage is applied to the cell in the atmospheric pressure measuring mode, and the time required to generate a given change (E=0.1 V) in the electromotive force of the concentration cell (before versus after pumping) is measured. In either of these methods, the accuracy, the response and the required time for atmospheric pressure detection are within the range of practical use.

By using the atmospheric pressure signal obtained in the atmospheric pressure measuring mode, the control parameter or the information parameter for an engine power train system such as fuel injection timing or ignition timing for a vehicle can be corrected, with the correction coefficient or correction function obtained from the experiment or the principle equations in advance using the micro-computer 18, for example, placed in an engine control unit 17. In this manner, the atmospheric pressure correction function can be provided without adding an atmospheric pressure sensor, even in a case of the control system with no atmospheric pressure detecting function.

By using the atmospheric pressure signal obtained in the above atmospheric pressure detecting process, the sensor output is corrected with the micro-computer 12 of the air-fuel-sensor, or by using the correction coefficient or the correction function obtained from the experiment or the principal equation in advance. The atmospheric pressure dependence of the fuel control (air-fuel ratio control) by the air-fuel ratio sensor is corrected by the micro-computer of the engine control unit 17. Thus, the atmospheric pressure dependence of the output of the air-fuel ratio sensor can be corrected and the accuracy in the air-fuel ratio control can be improved.

Outputting the air-fuel ratio signal and the atmospheric pressure signal separately in the atmospheric pressure detecting process, the atmospheric pressure signal may be applied to general purposes such as systems for display, information or safety as well as applied to the correction of engine parameters.

The atmospheric pressure detecting function can be added to an air-fuel ratio sensor without affecting the air-fuel ratio detecting function. Therefore, without any specific atmospheric pressure sensor, the atmospheric pressure dependence of an air-fuel ratio sensor can be corrected using only the function of the air-fuel ratio sensor itself; further, atmospheric pressure data can be also used to correct various operating conditions on the engine control when required.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Apparatus for measuring atmospheric pressure in conjunction with an air-fuel ratio sensor comprising:

a concentration cell having an atmospheric air side electrode and an exhaust gas side electrode arranged on opposite sides of a solid-state electrolyte having oxygen ion conductivity;

an exhaust gas diffusion rate control member covering said exhaust gas side electrode;

means for ionizing and pumping oxygen molecules between the atmospheric air side electrode and the exhaust gas side electrode;

means for controlling said pumping of ionized oxygen molecules to maintain an electromotive force to the concentration cell due to a ratio of oxygen partial pressure at said atmospheric air side electrode and said exhaust gas side electrode, at a set voltage level; and means for measuring pumping current due to said pumping of ionized oxygen molecules;

said apparatus comprising:

means for controlling said air-fuel ratio sensor to operate alternately in an air-fuel ratio detection mode and a separate atmospheric pressure measuring mode;

means operative during said atmospheric pressure measuring mode for controlling pumping of a quantity of ionized oxygen molecules from said atmospheric air side electrode to said exhaust gas side electrode, said quantity being one of: a set quantity and a quantity which achieves equilibrium of said concentration cell;

means operative during said atmospheric pressure measuring mode for measuring electromotive force of said concentration cell following completion of pumping of said quantity of ionized oxygen molecules; and means for calculating atmospheric pressure as a function of the electromotive force of the concentration cell measured after completion of pumping of said quantity of ionized oxygen molecules, said function having been experimentally determined.

2. Apparatus according to claim 1 wherein said means for calculating atmospheric pressure comprises a microcomputer and said function comprises an experimentally derived mathematical formula.

3. Apparatus according to claim 1 wherein said means for calculating atmospheric pressure comprises:

a microcomputer;

a memory storage device containing a look up table of experimentally determined atmospheric pressure values corresponding to given values of electromotive force of the concentration cell.

4. Apparatus according to claim 1 wherein said set quantity of ionized oxygen molecules is selected such that said electromotive force of the concentration cell measured by said means for measuring electromotive force falls within a range of from 0.05 V to 0.4 V at standard atmospheric pressure of 101.3 kPa.

5. Apparatus according to claim 1 wherein said second means for controlling causes said air-fuel ratio sensor to operate in said atmospheric measurement mode in response to a change in atmospheric pressure.

6. Apparatus according to claim 1 wherein said second means for controlling causes said air-fuel sensor to operate in said atmospheric pressure measuring mode in a time sharing sequence with said air-fuel ratio detecting mode after operation of said means for measuring pumping current.

7. Apparatus according to claim 1 further comprising:
means for adjusting operation of a system of a vehicle in response to measured atmospheric pressure.

8. Apparatus according to claim 1 further comprising:
means for correcting an output of said air-fuel ratio sensor in response to measured atmospheric pressure.

9. Apparatus for measuring atmospheric pressure in conjunction with an air-fuel ratio sensor comprising:
a concentration cell having an atmospheric air side electrode and an exhaust gas side electrode arranged on opposite sides of a solid-state electrolyte having oxygen ion conductivity;
an exhaust gas diffusion rate control member covering said exhaust gas side electrode;
means for ionizing and pumping oxygen molecules between the atmospheric air side electrode and the exhaust gas side electrode;
means for controlling said pumping of ionized oxygen molecules to maintain an electromotive force of the concentration cell due to a ratio of oxygen partial pressure at said atmospheric air side electrode and said exhaust gas side electrode, at a set voltage level; and
means for measuring pumping current due to said pumping of ionized oxygen molecules;
said apparatus comprising:
means for controlling said air-fuel ratio sensor to operate alternately in an air-fuel ratio detection mode and a separate atmospheric pressure measuring mode;
means operative during said atmospheric pressure measuring mode for controlling pumping of ionized oxygen molecules from said atmospheric air side electrode to said exhaust gas side electrode until an electromotive force of the concentration cell changes by a set amount;
means for measuring a period of time t required for pumping of ionized oxygen molecules until said electromotive force of the concentration cell changes by a predetermined amount;
means for calculating atmospheric pressure as a function of said period of time t, according to an experimentally determined functional relationship.

10. Apparatus according to claim 9 wherein said means for calculating atmospheric pressure comprises a microcomputer, and said functional relationship comprises an experimentally derived mathematical formula.

11. Apparatus according to claim 9 wherein said means for calculating comprises:
a microcomputer;
a memory storage device containing a lookup table of experimentally determined atmospheric pressure values corresponding to a plurality of values of time t.

12. Apparatus according to claim 9 wherein said second means for controlling causes said air-fuel ratio sensor to operate in said atmospheric measurement mode in response to a change in atmospheric pressure.

13. Apparatus according to claim 9 wherein said second means for controlling causes said air-fuel sensor to operate in said atmospheric pressure measuring mode in a time sharing sequence with said air-fuel ratio detecting mode after operation of said means for measuring pumping current.

14. Apparatus according to claim 9 further comprising:
means for adjusting operation of a system of a vehicle in response to measured atmospheric pressure.

15. Apparatus according to claim 5 further comprising:
means for correcting an output of said air-fuel ratio sensor in response to measured atmospheric pressure.

16. Method of measuring atmospheric pressure in conjunction with an air-fuel ratio sensor comprising:
a concentration cell having an atmospheric air side electrode and an exhaust gas side electrode arranged on opposite sides of a solid-state electrolyte having oxygen ion conductivity;
an exhaust gas diffusion rate control member covering said exhaust gas side electrode;
means for ionizing and pumping oxygen molecules between the atmospheric air side electrode and the exhaust gas side electrode;
means for controlling said pumping of ionized oxygen molecules to maintain an electromotive force of the concentration cell due to a ratio of oxygen partial pressure at said atmospheric air side electrode and said exhaust gas side electrode, at a set voltage level; and
means for measuring pumping current due to said pumping of ionized oxygen molecules;
said method comprising the steps of:
operating said air-fuel ratio sensor alternately in an air-fuel ratio detection mode and a separate atmospheric pressure measuring mode;
during said atmospheric pressure measuring mode, controlling pumping of a quantity of ionized oxygen molecules from said atmospheric air side electrode to said exhaust gas side electrode, said quantity being one of: a set quantity and a quantity which achieves equilibrium of said concentration cell;
measuring electromotive force of said concentration cell following completion of said step of controlling pumping; and
calculating atmospheric pressure as a function of the electromotive force of said concentration cell measured during said measuring step, said function having been experimentally determined.

17. Method of measuring atmospheric pressure in conjunction with an air-fuel ratio sensor comprising:
a concentration cell having an atmospheric air side electrode and an exhaust gas side electrode arranged on opposite sides of a solid-state electrolyte having oxygen ion conductivity;
an exhaust gas diffusion rate control member covering said exhaust gas side electrode;
means for ionizing and pumping oxygen molecules between the atmospheric air side electrode and the exhaust gas side electrode;
means for controlling said pumping of ionized oxygen molecules to maintain an electromotive force of the concentration cell due to a ratio of oxygen partial pressure at said atmospheric air side electrode and said exhaust gas side electrode, at a set voltage level; and means for measuring pumping current due to said pumping of ionized oxygen molecules;

said method comprising the steps of:

operating said air-fuel sensor alternately in an airfuel ratio detection mode and a separate atmospheric pressure measuring mode;

during said atmospheric pressure measuring mode, controlling pumping of ionized oxygen molecules from said atmospheric air side electrode to said exhaust gas side electrode until an electromotive force of the concentration cell changes by a set amount;

measuring a period of time t required for pumping of ionized oxygen molecules until said electromotive force of the concentration cell changes by said set amount;

calculating atmospheric pressure as a function of said period of time t, according to an experimentally determined functional relationship.

* * * * *